United States Patent [19]

Wagle et al.

[11] Patent Number: 4,786,282

[45] Date of Patent: Nov. 22, 1988

[54] BANDAGE FOR THE TOPICAL ADMINISTRATION OF CONTROLLED AMOUNTS OF NITROGLYCERIN OINTMENT

[75] Inventors: Sudhakar S. Wagle, Mequon; George R. Felt, Brown Deer; Herbert W. Borleis, Brookfield, all of Wis.

[73] Assignee: Adria Laboratories, Dublin, Ohio

[21] Appl. No.: 26,495

[22] Filed: Mar. 16, 1987

Related U.S. Application Data

[63] Continuation of Ser. No. 705,771, Feb. 26, 1985, abandoned.

[51] Int. Cl.[4] .................. A61F 13/00; A61L 15/00
[52] U.S. Cl. ........................... 604/307; 128/156
[58] Field of Search ............... 604/890, 896, 897, 304, 604/307; 128/156, 155

[56] References Cited

U.S. PATENT DOCUMENTS

| | | | |
|---|---|---|---|
| 4,341,208 | 7/1982 | Gordon | 604/897 |
| 4,460,370 | 7/1984 | Allison et al. | 604/897 |
| 4,619,654 | 10/1986 | Abplanalp | 604/897 |

Primary Examiner—C. Fred Rosenbaum
Assistant Examiner—Sharon Rose
Attorney, Agent, or Firm—John C. Smith, Jr.

[57] ABSTRACT

A bandage for the continuous administration of nitroglycerin to the skin comprising a backing member defining one exterior surface, an internal backing layer with calibrations thereon for accurate measurement of the amount of nitroglycerin ointment to be deposited thereon, an adhesive layer surrounding the internal backing layer for attachment to the skin, and a releasable backing member applied to the adhesive layer.

3 Claims, 2 Drawing Sheets

BANDAGE FOR THE TOPICAL ADMINISTRATION OF CONTROLLED AMOUNTS OF NITROGLYCERIN OINTMENT

This is a continuation of application Ser. No. 705,771 filed Feb. 26, 1985, now abandoned.

BACKGROUND OF THE INVENTION

Topical application of nitroglycerin to the skin for the treatment of both Raynaud's disease and angina pectoris is well known. Several investigators have described substantial improvement in the acrosclerosis associated with Raynaud's disease resulting from nitroglycerin.

The treatment of angina pectoris with nitroglycerin or rapid acting nitrites has been described by Davis et al in the *American Journal of the Medical Sciences*, Vol. 230, No. 3, September, 1955. In this article, the authors suggested that nitroglycerin ointment, because of the slowed absorption through the skin, might result in the superior vasodilating effect of the nitroglycerin being prolonged in relation to coronary circulation. They reported that the results were dramatic and convincing enough that they have instituted nitroglycerin ointment treatment on a regular basis.

SUMMARY OF THE INVENTION

It is an object of this invention to provide a bandage for the continuous administration of a predetermined quantity of nitroglycerin, through the skin, over a period of time.

Another object of the invention is to provide a bandage in which the quantity of nitroglycerin ointment can be easily determined and controlled.

In accomplishing these objects, one feature of the invention is the preparation of a bandage that includes an external moisture-impervious backing and a smaller internal backing having calibrations thereon. The calibrations may be of different types and afford the doctor and patient a convenient and accurate method of measuring the amount of nitroglycerin ointment applied to the bandage. The surface area of the internal backing of the bandage is set so that a therapeutically useful amount of drug will be delivered transdermally to the patient after the drug has been measured onto the internal backing and the bandage applied to the skin of the patient. The internal backing is surrounded by an adhesive layer applied to the external backing and is covered with a detachable or releasable backing that can be removed to expose the adhesive layer for convenient attachment to the skin. The bandage may also include a removal tab to simplify stripping the bandage from the skin.

DETAILED DESCRIPTION OF THE INVENTION

In accordance with this invention, there is provided a bandage suitable for retaining nitroglycerin ointment used for topical treatment of Raynaud's disease and angina pectoris. Normally, a 2% nitroglycerin ointment is used.

To use the bandage the desired amount of nitroglycerin ointment is conveniently extruded from a tube onto the calibrated area on the internal backing. The dosage of nitroglycerin ointment may be controlled conveniently by extending a predetermined length and width of the nitroglycerin ointment as measured by the calibration on the internal backing.

After the desired amount of nitroglycerin ointment has been applied to the internal backing, the release backing surrounding the internal backing is removed to expose the adhesive layer.

The bandage is then applied to the skin of the patient and pressed down firmly to assure that the adhesive is attached to the skin.

At the end of the treatment the bandage can be removed by grasping a skin removal tab at the edge of the bandage and separaing the bandage from the skin.

Figure 1:
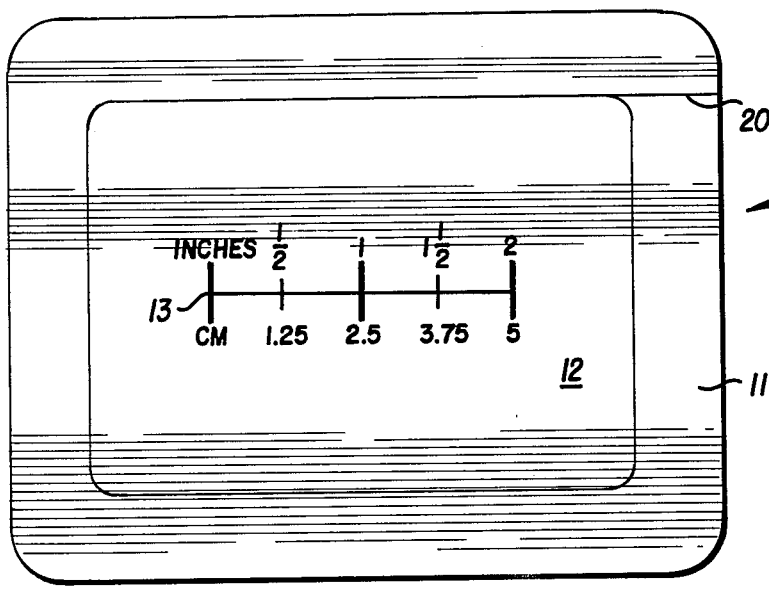
FIG. 1 is a front view of one embodiment of the bandage of the instant invention showing one type of calibration on the internal backing and one type of release backing.
Figure 2:
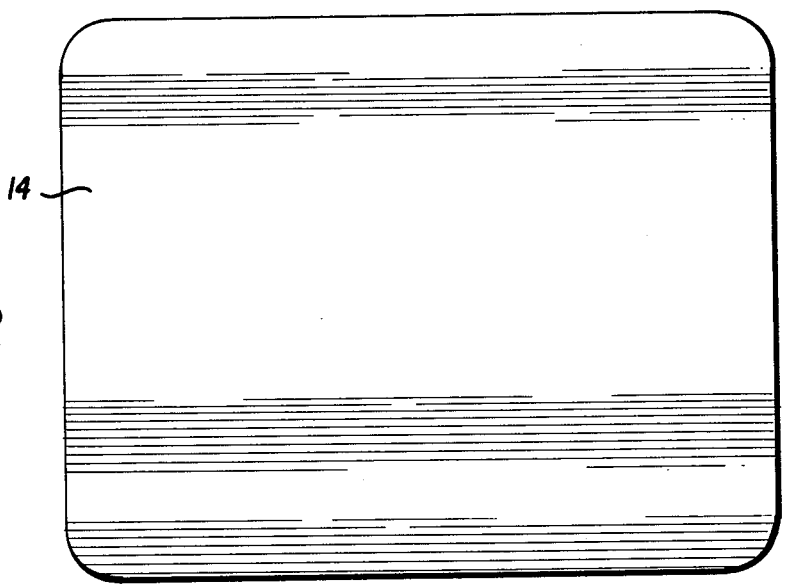
FIG. 2 is a rear view of the bandage of FIG. 1.
Figure 3:
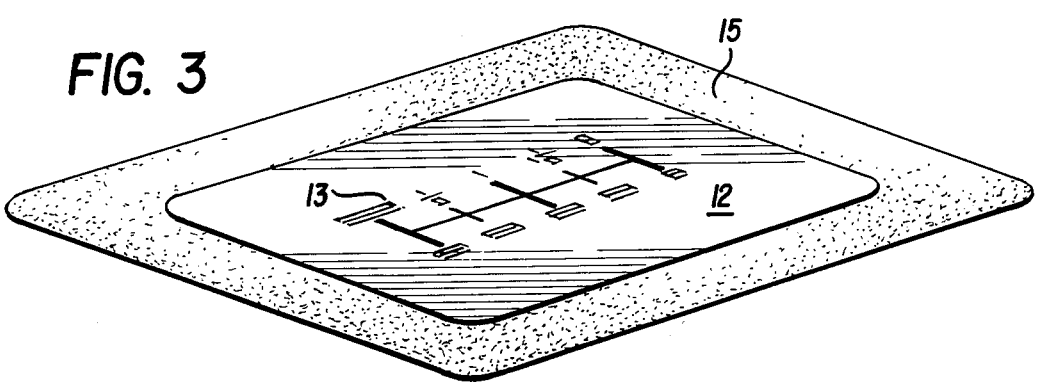
FIG. 3 is a perspective view of the bandage of FIG. 1 with the release backing removed and the adhesive layer exposed.

FIGS. 1 and 2 are front and rear views of one embodiment of the bandage 10 of the invention. The bandage comprises an overall backing 14, an internal backing 12 secured to one side of the overall backing 14 and a release backing 11 releasably secured to the overall backing 14 about the perimeter of the internal backing 12. The internal backing 12 and release backing 11 may be secured conveniently to the overall backing by first applying a releasable adhesive to the entirety of one surface of the overall backing 14 and then applying the internal backing 12 and releasable backing 11 to the adhesive surface. A portion of the adhesive surface 15 applied to the overall backing 14 is shown in FIG. 3.

The overall backing 14 is a conventional polymeric plastic film such as a vinyl film commonly used in bandages.

The adhesive layer 15 should be composed of a hypoallergenic material such as an acrylic adhesive commonly used in adhesive coated bandages.

The releasable backing 11 may be composed of paper material having a conventional silicone-containing release material on the surface thereof in contact with the adhesive layer 15. The releasable backing 11 has a cut 20 to permit easier removal of the releasable backing from the adhesive layer 15.

The internal backing 12 may be composed of the same paper material as the releasable backing 11. The paper material should alow only minimal absorbency of the nitroglycerin ointment.

Calibration indicia are printed on the exposed surface of the internal backing layer 12. FIGS. 1 and 3 illustrate one form of the calibration indicia for measuring the amount of nitroglycerin ointment to be applied to the internal backing layer 12.

Figure 4:
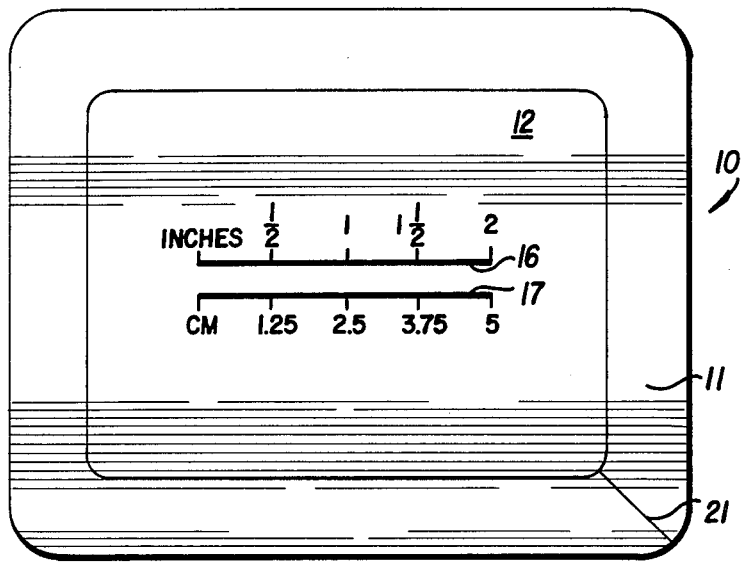
FIG. 4 is a front view of another embodiment of the instant invention showing another type of calibration on the internal backing and another type of release backing.
Figure 5:
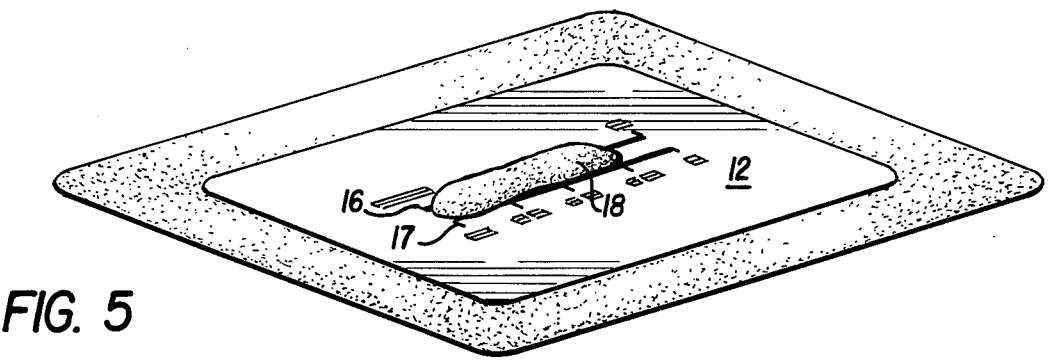
FIG. 5 is a perspective view of the bandage of FIG. 4 with the release backing removed and the adhesive layer exposed and with nitroglycerin ointment applied to the internal backing.

FIGS. 4 and 5 illustrate another embodiment of the bandage 10. The features of this embodiment, which are the same as the features of the embodiment illustrated in FIGS. 1 to 3, are identified by the same numerical designations. In the embodiment illustrated in FIGS. 4 and 5, the cut 21 in the releasable backing member 11 is located at a corner of the bandage to facilitate removal of the releasable backing 11 from the adhesive layer 15. Also the calibrated indicia comprise two spaced parallel lines with calibrations in inches on one line and in centimeters on the other line. The width of the space between the lines is generally the width of the ointment tube opening and the ribbon of nitroglycerin ointment thereby allowing exact measurement of the dose with minimum variability. The ribbon of nitroglycerin ointment 18 is applied between the two parallel lines as is illustrated in FIG. 5.

Figure 6:
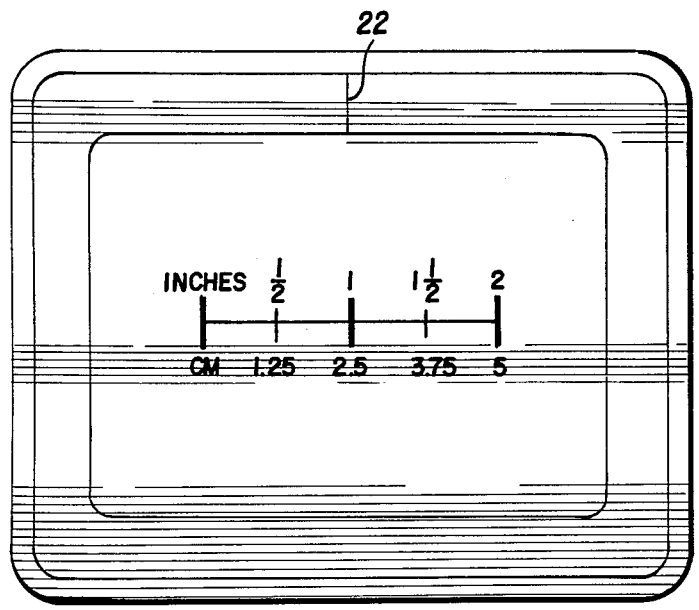
FIG. 6 is a front view of still another embodiment of the bandage of the instant invention.

FIG. 6 illustrates a further embodiment of the bandage 10. In this instance the releasable backing 11 surrounding the internal backing 12 is narrower than the releasable backings illustrated in FIGS. 1 and 4 such that the overall backing 14 extends beyond the perimeter of the releasable backing 11. The adhesive layer 20 applied to the overall backing 14 does not extend beyond the perimeter of the releasable backing 11 to provide a continuous tab about the perimeter of the overall backing 14 which may be gripped easily to strip the bandage from the skin. The cut 22 in the releasable backing 11 is located intermediate opposite ends of the bandage.

Production of bandages in accordance with the present invention is carried out by coating vinyl film with a hypoallergenic medical grade adhesive and then laminating the coated vinyl to a release coated paper liner. The vinyl/adhesive/release liner is wound into rolls, cut to width and rewound into rolls. The rolls are then appropriately printed and die cut. Differential die cutting is performed so that a band of releasable paper backing 11 can be peeled away to expose adhesive whereby the bandage can be secured to the patient. Differential die cuts 20, 21, or 22 are made to facilitate the removal of the releasable backing 11. The bandages may be die cut so that they are produced in individual units; or perforations may be cut between individual bandages so that a roll of bandages can be produced such that as a bandage is needed it is torn away from the roll along the perforations.

Obviously, modifications and variations of the invention may be made without departing from the essence and scope thereof, and only such limitations shall be applied as are indicated in the appended claims.

What is claimed is:

1. A laminated medicinal bandage for the continuous administration of controlled quantities of ointment, such as nitroglycerin, to the skin or mucosa and consisting of two layers:
   (a) the first layer comprising a backing sheet member having oppositely facing surfaces and predetermined perimeter dimensions and having a layer of adhesive on one of said surfaces thereof;
   (b) the second layer comprising:
      1. an internal backing sheet member having predetermined perimeter dimensions less than those of said backing sheet member and having a calibrated scale on one surface thereof for accurate measurement of an ointment dosage applied thereto and adapted for contacting the skin, the surface of said internal backing sheet member opposite said one surface thereof being secured by said adhesive layer on said one surface of said backing sheet member in a position thereon such that an annular portion of said adhesive layer on said one surface of said backing sheet member extends about the perimeter of said internal backing sheet member between the respective perimeters of said internal backing sheet member and said first layer; and
      2. an annular releasable backing layer covering said annular portion of said adhesive layer and surrounding the perimeter of said internal backing sheet member, said releasable backing layer and said internal backing sheet member being in the same plane and composed of the same material;
   (c) whereby said annular releasable backing layer may be removed and said bandage, with the ointment on said surface of said internal backing sheet member, secured in place on the skin by said annular portion of said adhesive on said one surface of said backing sheet member.

2. The laminated medicinal bandage according to claim 1 wherein said internal backing sheet member carries two calibrated scales spaced from each other, the calibration of each scale being different from the calibration of the other scale.

3. In a method for the topical treatment of angina pectoris and Raynaud's disease wherein nitroglycerin ointment is used locally to provide a systemic effect in the treatment, the improvement which consists of administering controlled quantities of nitroglycerin ointment to the skin or mucosa from a laminated medicinal bandage attached to the skin of a patient, said laminated medicinal bandage consisting of two layers:
   (a) the first layer comprising a backing sheet member having oppositely facing surfaces and predetermined perimeter dimensions and having a layer of adhesive on one of said surfaces thereof;
   (b) the second layer comprising:
      1. an internal backing sheet member having predetermined perimeter dimensions less than those of said backing sheet member and having a calibrated scale on one surface thereof for accurate measurement of an ointment dosage applied thereto and adapted for contacting the skin, the surface of said internal backing sheet member opposite said one surface thereof being secured by said adhesive layer on said one surface of said backing sheet member extends about the perimeter of said internal backing sheet member between the respective perimeters of said internal backing sheet member and said first layer; and
      2. an annular releasable backing layer covering said annular portion of said adhesive layer and surrounding the perimeter of said internal backing sheet member, said releasable backing layer and said internal backing sheet member being in the same plane and composed of the same material;
   (c) whereby said annular releasable backing layer may be removed and said bandage, with the ointment on said surface of said internal backing sheet member, secured in place on the skin by said annular portion of said adhesive on said one surface of said backing sheet member.

* * * * *